(12) United States Patent  (10) Patent No.: US 9,316,594 B2
Kane  (45) Date of Patent: Apr. 19, 2016

(54) CARBON DIOXIDE ($CO_2$) SENSOR

(71) Applicant: James A. Kane, Needham Heights, MA (US)

(72) Inventor: James A. Kane, Needham Heights, MA (US)

(73) Assignee: Polestar Technologies, Inc., Needham Heights, MA (US)

( * ) Notice: Subject to any disclaimer, the term of this patent is extended or adjusted under 35 U.S.C. 154(b) by 0 days.

(21) Appl. No.: 13/905,639

(22) Filed: May 30, 2013

(65) Prior Publication Data

US 2013/0323845 A1  Dec. 5, 2013

Related U.S. Application Data

(60) Provisional application No. 61/654,219, filed on Jun. 1, 2012.

(51) Int. Cl.
*G01N 21/80* (2006.01)
*A61B 5/1455* (2006.01)
*G01N 31/22* (2006.01)
*G01N 21/78* (2006.01)
*A61B 5/1491* (2006.01)

(52) U.S. Cl.
CPC ............ *G01N 21/80* (2013.01); *A61B 5/14551* (2013.01); *A61B 5/14552* (2013.01); *G01N 21/783* (2013.01); *G01N 31/223* (2013.01); *A61B 5/1491* (2013.01)

(58) Field of Classification Search
CPC ... G01N 21/80; G01N 21/783; G01N 31/223; A61B 5/1491; A61B 5/14552; A61B 5/14551

USPC .............. 422/425; 436/170, 425, 68; 435/6.11
See application file for complete search history.

(56) References Cited

U.S. PATENT DOCUMENTS

| | | | |
|---|---|---|---|
| 5,472,668 A * | 12/1995 | Mills et al. | 422/425 |
| 5,480,611 A | 1/1996 | Mills et al. | |
| 5,849,594 A | 12/1998 | Balderson et al. | |
| 2003/0003593 A1 * | 1/2003 | Wallach | 436/170 |
| 2013/0078624 A1 * | 3/2013 | Holmes et al. | 435/6.11 |

OTHER PUBLICATIONS

Chang et al. Steam-Sterilizable, Fluorescence Lifetime-Based Sensing Film for Dissolved Carbon Dioxide.*
Chang, Q. et al. Fluorescence Lifetime-Based Sensing Film for Dissolved Carbon Dioxide, Biotechnol. Prog., 14 (2), 326-331, 1998.

* cited by examiner

*Primary Examiner* — Rebecca M Fritchman
(74) *Attorney, Agent, or Firm* — Burns & Levinson LLP; Orlando Lopez

(57) ABSTRACT

A carbon dioxide detector including a sensor component, where the sensor component has a colorimetric indicator salt of a colorimetric pH indicator and a lipophilic phosphonium quaternary cation, a transparent polymer vehicle or a plasticizer not being in a mixture with the colorimetric indicator salt; and a porous memory, a porous polymer membrane in one instance, the colorimetric indicator salt being deposited on a surface of the porous polymer membrane; the colorimetric indicator salt deposited on the porous polymer membrane does not include a transparent polymer vehicle or a plasticizer, and carbon dioxide detection systems using the detector.

33 Claims, 11 Drawing Sheets

US 9,316,594 B2

CARBON DIOXIDE ($CO_2$) SENSOR

CROSS REFERENCE TO RELATED APPLICATIONS

This application claims priority to U.S. Provisional Application Ser. No. 61/654,219, filed on Jun. 1, 2012, entitled, "CARBON DIOXIDE (CO2) SENSOR," which is incorporated by reference herein in its entirety for all purposes.

STATEMENT REGARDING FEDERALLY SPONSORED RESEARCH OR DEVELOPMENT

This invention was made partially with U.S. Government support from the U.S. Navy under contract N0463A-10-C-004, from the U.S. Army under contract W81XWH-10-C-0039. The U.S. Government has certain rights in the invention.

BACKGROUND

This invention relates generally to carbon dioxide ($CO_2$) sensors.

Electrochemical $CO_2$ sensor using a Severinghaus electrode are known. Although widely accepted for measurements of dissolved $CO_2$, the Severinghaus type sensor is not suitable for gas phase measurements. Sensor drift arising from loss of electrolyte by evaporation or failure due to puncture of the sensor's Teflon membrane are among the most serious factors limiting the use of this type of sensor. A number of sensors are commercially available for gas phase measurements of $CO_2$ based on non-dispersive infrared (IR) absorption. Gaseous $CO_2$ exhibits a characteristic absorption band in the mid-IR that can be used to determine gas phase concentrations according to Beer's law. Although sensitive, the IR devices require expensive detectors and light sources, and must include sample cell heaters or water vapor filters under conditions where water condensation can occur in order to avoid interference in their readings.

$CO_2$ sensors that provide a detectable indication of the presence of an elevated proportion of carbon dioxide in gaseous state, where the sensor has a substrate coated by an intimate mixture of a transparent plasticised polymer vehicle, and an indicator material which undergoes a color change on exposure to carbon dioxide, the mixture disposed over a substrate, have been disclosed.

There is a need for $CO_2$ sensors for carbon dioxide in gaseous state, where the sensor does not need a transparent polymer vehicle or a plasticizer and the sensor is easily read.

Two exemplary embodiments of applications where there is a need for improved $CO_2$ sensors are described below.

The role of arterial carbon dioxide on vasodilation makes it a critical parameter in controlling tissue perfusion and oxygen delivery particularly during prehospital care of patients requiring mechanical ventilation. Proper ventilation leading to early correction and/or maintenance at normocapnia levels in patients with severe traumatic brain injury has been shown to significantly reduce mortality rates in these high risk subjects. These results support the development of improved ambulatory mechanical ventilation technologies including the development of more accurate noninvasive means of estimating $PaCO_2$.

Presently, the existing methods for noninvasive estimation of $PaCO_2$ include measurements of end-tidal carbon dioxide ($PETCO_2$) or transcutaneous $CO_2$ sensing electrodes. Issues with correlation and/or accuracy in comparative studies against invasive blood gas analysis have raised questions about the utility of these devices, particularly when applied to adult subjects. Discrepancies between $PETCO_2$ readings and $PaCO_2$ measurements by blood gas analyzers are primarily attributed to the presence of pulmonary dead space volume and physiological conditions that can exacerbate dead space volume including obstructive pulmonary pathology, hypovolemia, atelectasis and mechanical ventilation. Studies of Severinghaus-type transcutaneous $CO_2$ electrodes have shown better correlation with blood gas analysis (BGA) values, but there remain problems with inaccuracies arising from calibration drift due to evaporative loss of electrolyte and slow response times which introduce a time lag in readings taken with this type of sensor. The use of localized heating has long been used to improve the response time of transcutaneous sensors by increasing arterilization and epidermal permeability in the area under investigation. However, local heating does not appreciably reduce the two to three minute response times of $CO_2$ electrodes which introduces a time lag in readings that can be misinterpreted as an error when compared with BGA readings especially if blood samples occurs during a period of rapid change in the arterial CO-level. A $CO_2$ gas sensor that can be reliably used for noninvasive monitoring of arterial $CO_2$ does not exist and new ways to approach the problem are needed.

In another exemplary embodiment, $CO_2$ sensors find applications in rebreathers used by divers. Divers use a closed circuit Underwater Breathing Apparatus (UBA), also known as rebreather, for many of their deep diving operations and for training. Although there are several design variations of the diving rebreather, all types have a gas-tight loop that the diver inhales from and exhales into. The diver breathes through a mouthpiece that is connected to one or more tubes bringing inhaled gas and exhales gas to a breathing bag. The loop also includes a scrubber containing carbon dioxide absorbent to remove from the loop the carbon dioxide ($CO_2$). The exhaled gases are forced through the chemical scrubber which removes the carbon dioxide from the gas mixture and leaves the oxygen and other gases available for re-breathing. Scrubber failure, which can result from many causes, leads to black-out and hence is very dangerous to the diver. It would be very useful to monitor the $CO_2$ in the rebreather so that the scrubber can be replaced before the $CO_2$ levels get dangerously high. Currently, no such $CO_2$ sensor exists for the use of deep sea divers.

There is a need for $CO_2$ sensors for carbon dioxide in gaseous state, where the sensor does not need a transparent polymer vehicle or a plasticizer and the sensor is easily read, has a fast response time can be reliably used for noninvasive monitoring.

BRIEF SUMMARY

In one embodiment, the sensor of these teachings includes the salt of a colorimetric pH indicator (D) and lipophilic phosphonium quaternary cation (Q+) deposited on a surface of a pore structure of a porous polymer membrane, where a transparent polymer vehicle or a plasticizer are not used.

In one or more embodiments, the carbon dioxide detector of these teachings includes a sensor component, where the sensor component has a colorimetric indicator salt of a colorimetric pH indicator and a lipophilic phosphonium quaternary cation, a transparent polymer vehicle or a plasticizer not being in a mixture with the colorimetric indicator salt; and a porous memory, a porous polymer membrane in one instance, the colorimetric indicator salt being deposited on a surface of the porous polymer membrane; the colorimetric indicator salt deposited on the porous polymer membrane does not include a transparent polymer vehicle or a plasticizer.

In one or more embodiments, the carbon dioxide detection system of these teachings includes a light emitting component emitting radiation at a range of wavelengths, the carbon dioxide detector of these teachings wherein the sensor component is disposed to receive the radiation emitted by the light emitting component, the range of wavelengths being selected to include wavelengths in an absorption spectrum of the colorimetric indicator salt, and a detector component configured to receive radiation after an interaction with the sensor component, where the interaction can be transmission or scattering.

In one or more embodiments, the method of these teachings for forming a carbon dioxide detector includes mixing a colorimetric pH indicator, at a molar concentration for a desired colorimetric indicator salt, and a quaternary phosphonium hydroxide, at a slight molar excess, in a solvent, a transparent polymer vehicle or a plasticizer not being in a mixture with the colorimetric indicator salt, soaking a porous polymer membrane in the colorimetric indicator salt, quaternary phosphonium hydroxide, methanol solution for a predetermined length of time and evaporating the solvent.

Other embodiments of detectors, systems and method are disclosed hereinbelow.

For a better understanding of the present teachings, together with other and further objects thereof, reference is made to the accompanying drawings and detailed description and its scope will be pointed out in the appended claims.

DETAILED DESCRIPTION

Figure 1:
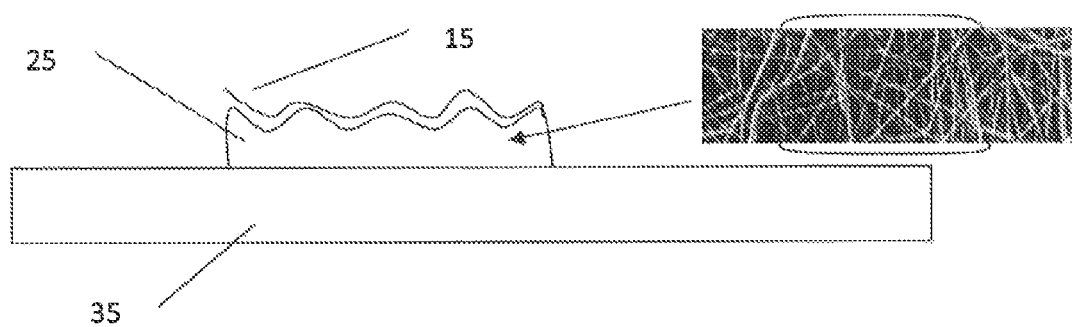
FIG. 1 is a schematic representation of one embodiment of the carbon dioxide detector of these teachings.

The following detailed description presents the currently contemplated modes of carrying out the invention. The description is not to be taken in a limiting sense, but is made merely for the purpose of illustrating the general principles of the invention, since the scope of the invention is best defined by the appended claims.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about."

In one or more embodiments, the sensor of these teachings includes a salt of a colorimetric pH indicator (D) and lipophilic phosphonium quaternary cation (Q+) deposited on a surface of a pore structure of a porous polymer membrane, where a transparent polymer vehicle or a plasticizer are not used.

In one or more embodiments, the carbon dioxide detector of these teachings includes a sensor component, where the sensor component has a colorimetric indicator salt of a colorimetric pH indicator and a lipophilic phosphonium quaternary cation, a transparent polymer vehicle or a plasticizer not being in a mixture with the colorimetric indicator salt; and a porous membrane, a porous polymer membrane in one instance, the colorimetric indicator salt being deposited on a surface of the porous polymer membrane; the colorimetric indicator salt deposited on the porous polymer membrane does not include a transparent polymer vehicle or a plasticizer.

In one instance, the porous polymer membrane is a nylon membrane. It should be noted that these teachings are not limited to a nylon membrane. A number of other porous materials are within the scope of these teachings. For example, other porous polymers such as, but not limited to, polysulfone, polyethersulfone, porous olefins such as some versions of Tyvek, and porous polypropylene, polyether ether ketone (PEEK), polyvinylidene difluoride, and polytetrafluoroethylene are within the scope of these teachings. In some instances, other porous materials, such as, porous ceramics and metals may be within the scope of these teachings.

Conventional carbon dioxide detector have a sensor component including a mixture of a polymer vehicle and an indicator salt (for examples of polymer vehicles see, for example, U.S. Pat. No. 5,480,611, which is incorporated by reference herein in its entirety and for all purposes). In the conventional carbon dioxide detector, whether or not the polymer vehicle includes a plasticizer depends on whether it is desirable for the detector to have substantially similar response ("rise") and recovery ("fall") time, in which case a plasticizer is added, or not to have substantially similar rise and fall times, in which case the polymer vehicle is non-plasticized.

The sensor component of these teachings does not have either a plasticizer or a polymer vehicle and exhibits substantially similar rise and fall times.

In one or more instances, the carbon dioxide detector of these teachings also includes a hydrophobic barrier, where the sensor component is disposed on the hydrophobic barrier.

One embodiment of the carbon dioxide detector of these teachings is shown in FIG. 1. Referring to FIG. 1, in the embodiment shown there in a colorimetric indicator salt 15 is deposited on a porous polymer membrane 25. The porous polymer membrane is disposed on a hydrophobic layer 35. It should be noted that the porous polymer membrane 25 is shown in a schematic form in order to show the colorimetric indicator salt being deposited on. In the insert, an actual porous polymer membrane is shown.

In one instance, the hydrophobic barrier is a nonwoven layer of spunbond olefin fibers or porous polypropylene (such as Tyvek® 1073B). It should be noted that other hydrophobic barriers are within the scope of these teachings.

In one instance, the sensor component is configured such that a response ("rise") time and a recovery ("fall") time of the carbon dioxide detector are substantially similar. For some embodiments, the response ("rise") time and the recovery ("fall") time of the carbon dioxide detector of these teachings is between about 7 to about 10 seconds.

In one or more embodiments, the colorimetric pH indicator is thymolsulfonephthalein (Thymol Blue), m-cresolsulfonephthalein (Meta Cresol purple), o-cresolsulfonephthalein (Cresol Red), bromothymol sulfone phthalein (Bromothymol Blue) or p-Xylenolsulfonephthalein (Xylenol Blue). It should be noted that these teachings are not limited only to these colorimetric pH indicators. In other embodiments, the colorimetric pH indicator is, for example, but not limited to, dibromo-o-cresolphthalein (bromocresol purple), tetrabromophenolsulfophthalein (bromophenol blue), phenolsulfophthalein (phenol red), thymolphthalein, o-cresolphthalein or phenolphthalein.

In one instance, the carbon dioxide detector of these teachings also includes a substantially non-porous layer disposed on the hydrophobic barrier and surrounding the sensor component. In one embodiment, the substantially non-porous layer comprises low-density polyethylene.

Figure 3A:
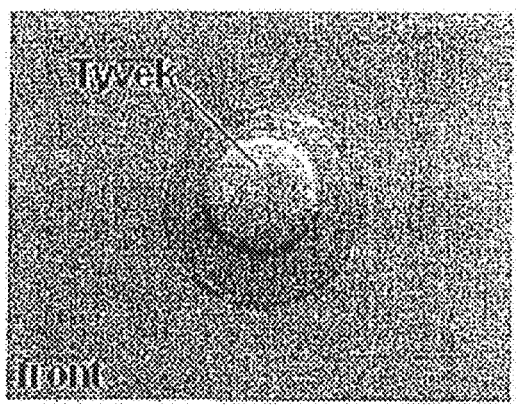
FIGS. 3a-3b show a top and bottom view of another embodiment of the carbon dioxide detector of these teachings.
Figure 3B:
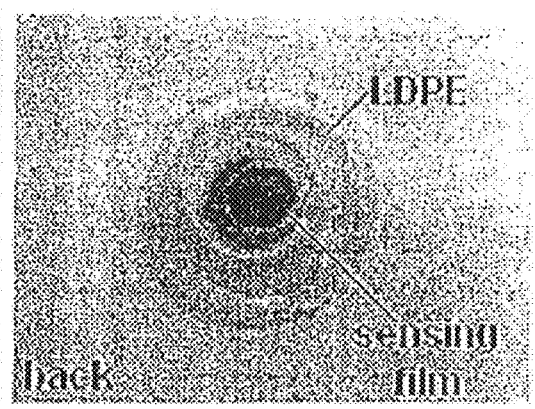

An embodiment of the carbon dioxide detector of these teachings is shown in FIGS. 3a and 3b. Referring to FIGS. 3a and 3b, in the embodiment shown there in, the $CO_2$ sensing film is configured within an envelope consisting of a porous polypropylene top layer (Tyvek), on which the sensor component is disposed, and a transparent, non porous low density polyethylene bottom layer (LDPE) formed by an annular heat seal around a disk of the sensor component (membrane).

The sensor component is based on the colorimetric $CO_2$ indicator salt formed from a quaternary phosphonium hydroxide and a weakly acidic phenolic-type pH sensitive dye. The indicator salt is immobilized in a highly porous polymeric membrane which allows $CO_2$ gas to rapidly diffuse into the membrane where it interacts with waters of hydration associated with the indicator salt yielding a molecule of carbonic acid that displaces the ammonium cation ($Q^+$) leading to protonation of the pH sensitive portion of the indicator (D) with changes to the spectral properties of the colorimetric indicator salt.

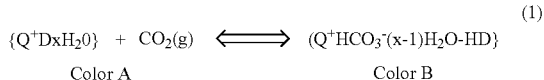

$$\{Q^+DxH_2O\} + CO_2(g) \Longleftrightarrow (Q^+HCO_3^-(x-1)H_2O\text{-}HD) \tag{1}$$

Color A  Color B

Figure 5:
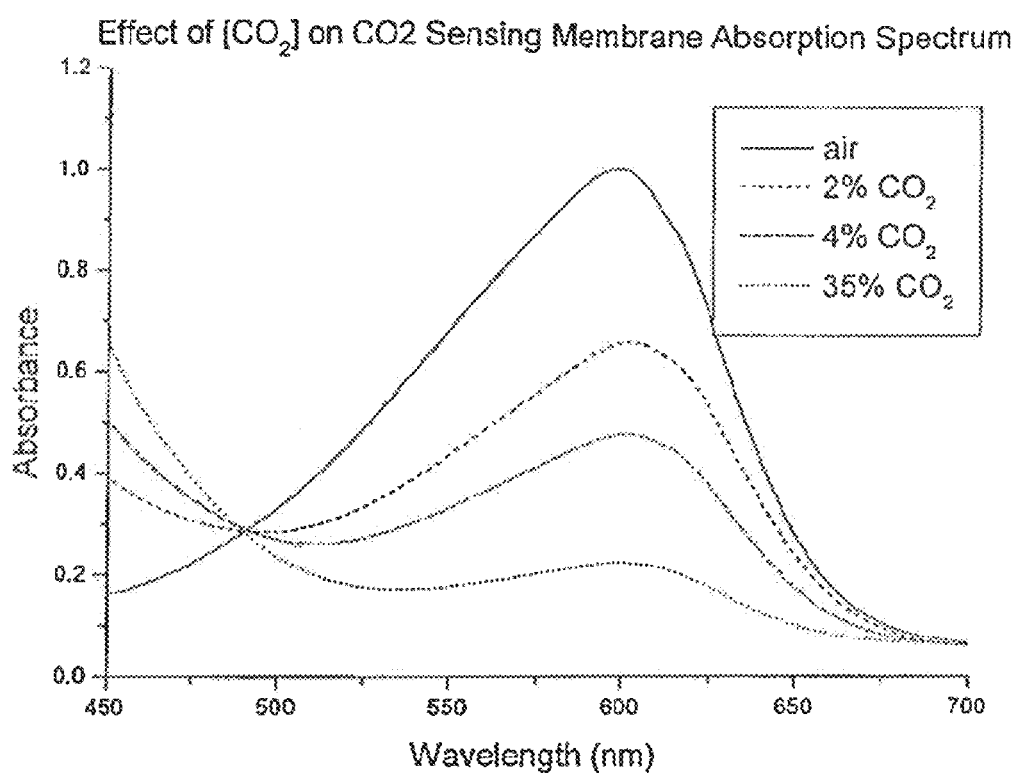
FIG. 5 depicts Absorbance spectra for an embodiment of a sensor of these teachings, having phosphonium salt of meta cresol purple immobilized in porous nylon membrane, during exposure to gaseous mixtures of $CO_2$ and air.

The $CO_2$-dependent shift in the equilibrium of expression (1) enables $CO_2$ levels to be determined from spectroscopic measurements (measurements of the change in spectral properties) as shown in FIG. 5, where the absorbance vs. $CO_2$ concentration is shown for the exemplary embodiment of a colorimetric indicator salt form from m-Cresol Purple.

The carbon dioxide detection system of these teachings detects the change in spectral properties of the colorimetric indicator salt of these teachings in induced by the $CO_2$ levels. In one or more embodiments, the carbon dioxide detection system of these teachings includes a light emitting component emitting radiation at a range of wavelengths, the carbon dioxide detector of these teachings wherein the sensor component is disposed to receive the radiation emitted by the light emitting component, the range of wavelengths being selected to include wavelengths in an absorption spectrum of the colorimetric indicator salt, and a detector component configured to receive radiation after an interaction with the sensor component, where the interaction can be transmission or scattering.

Figure 2A:
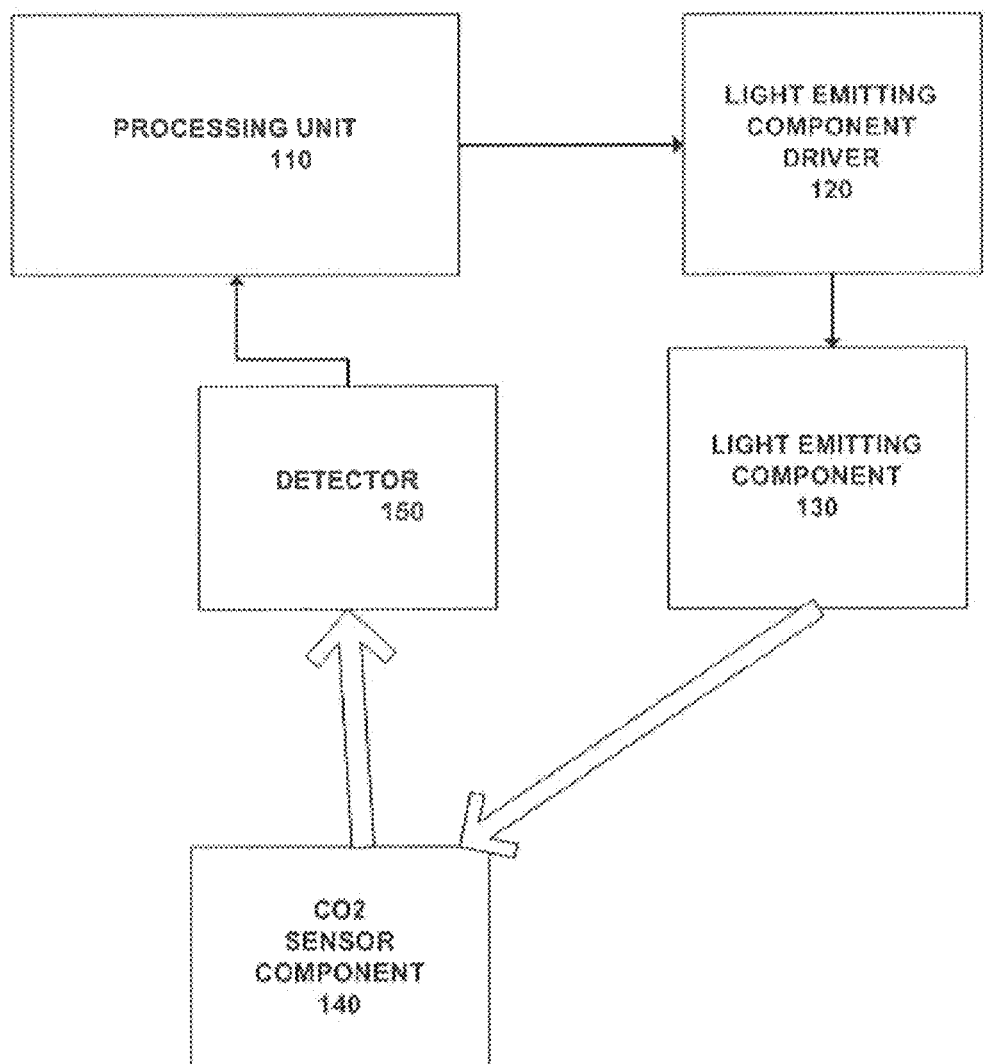
FIGS. 2a-2d show block diagram representations of embodiments of the carbon dioxide detection system of these teachings.

A block diagram of an embodiment of the carbon detection system of these teachings is shown in FIG. 2a. Referring to FIG. 2a, in the embodiment shown therein, the light emitting component 130 emits electromagnetic radiation that is received by the carbon dioxide sensor component 140. The electromagnetic radiation emitted by the light emitting component 130 interacts with the carbon dioxide sensor component 140, either by transmission or scattering, and the electromagnetic radiation, after the interaction, is received by the detector 150. Although the detector 150 is shown above the carbon dioxide sensor component 140, as would be the case where the interaction is scattering, the detector 150 can also be placed below the carbon dioxide sensor component 140, as would be the case where the interaction is transmission. A processing unit 110 is operatively connected to the detector 150 and to a light emitting component driver 120. The light emitting component driver 120 provides voltage or/and current to the light emitting component 130. The processing unit 110 controls the light emitting component 130 through the driver 120 and processes the output of the detector 150 in order to provide a determination of the $CO_2$ level. In one instance, the light emitting component 130 is a white LED and the detector is an image acquisition device capable of acquiring an image at three or more wavelengths (colors), for example, not a limitation of these teachings, the image acquisition device in a digital camera.

Figure 2B:
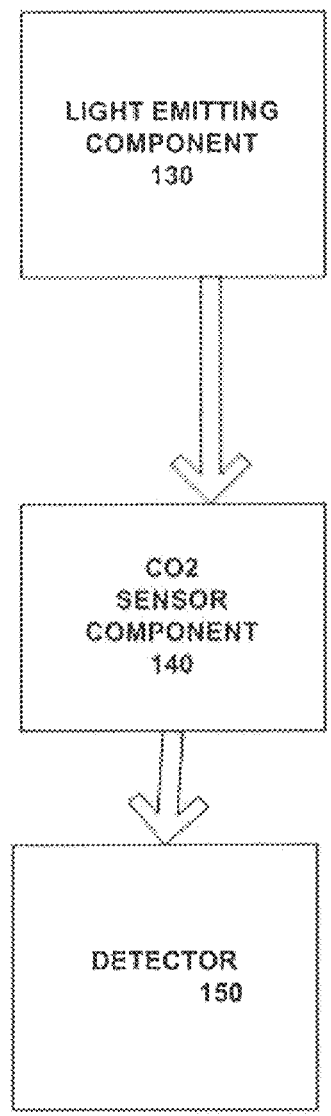

Another embodiment of the carbon dioxide detector system of these teachings, in which the interaction between the emitted radiation and the carbon dioxide sensor component 140 is transmission, is shown in FIG. 2b. Referring to FIG. 2b, in the embodiment shown there in, electromagnetic radiation emission from the light emitting component 130 impinges on the carbon dioxide sensor component 140 is transmitted through to the detector 150.

Figure 2C:
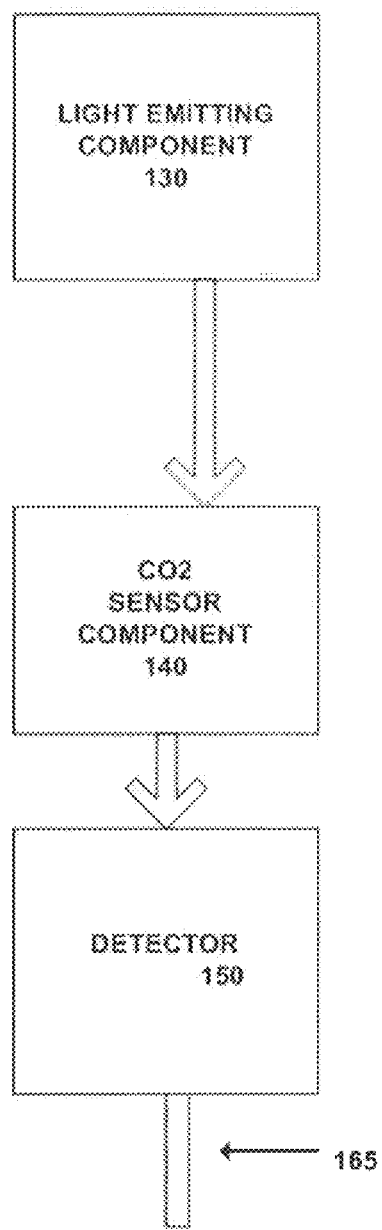

In one instance of the carbon dioxide detector system of these teachings, emission, from the light emitting component 130, in the range of wavelengths is substantially peaked at one color. In that instance, the light emitting component 130 and the sensor component 140 are disposed such that electromagnetic radiation emitted from the light emitting component 130 is transmitted through the sensor component 140 (the carbon dioxide sensor). In one embodiment, the carbon dioxide sensor of these teachings is disposed above the light emitting component and the carbon dioxide sensor is in substantially unobstructed optical communication with the light emitting component 130. The presence of a predetermined amount of carbon dioxide in the ambient causes a change in transmission of emission from the light emitting component. In another embodiment of the present instance, of the carbon dioxide detector system of these teachings also includes a driver circuit providing a driving voltage for the light emitting device and a negative temperature coefficient thermistor component operatively connected to the light emitting component and configured to adjust a current through the light emitting component in order to match temperature sensitivity of the carbon dioxide sensor. In one embodiment, when the carbon dioxide is less than the predetermined amount, the sensor component absorbs an amount of the emission from the light emitting component sufficient to make the emission from the light emitting component substantially unobservable. The change in transmission causes the emission from the light emitting component to be substantially unabsorbed by the carbon dioxide sensor. In one instance, the transmissions through the sensor component illuminates a fiber-optic cable (165, FIG. 2c), the fiber optic cable propagating the emission of the light emitting device. In one exemplary embodiment, the colorimetric pH indicator is p-Xylenolsulfonephthalein (Xylenol Blue); and wherein the light emitting device is a red LED.

Figure 2D:
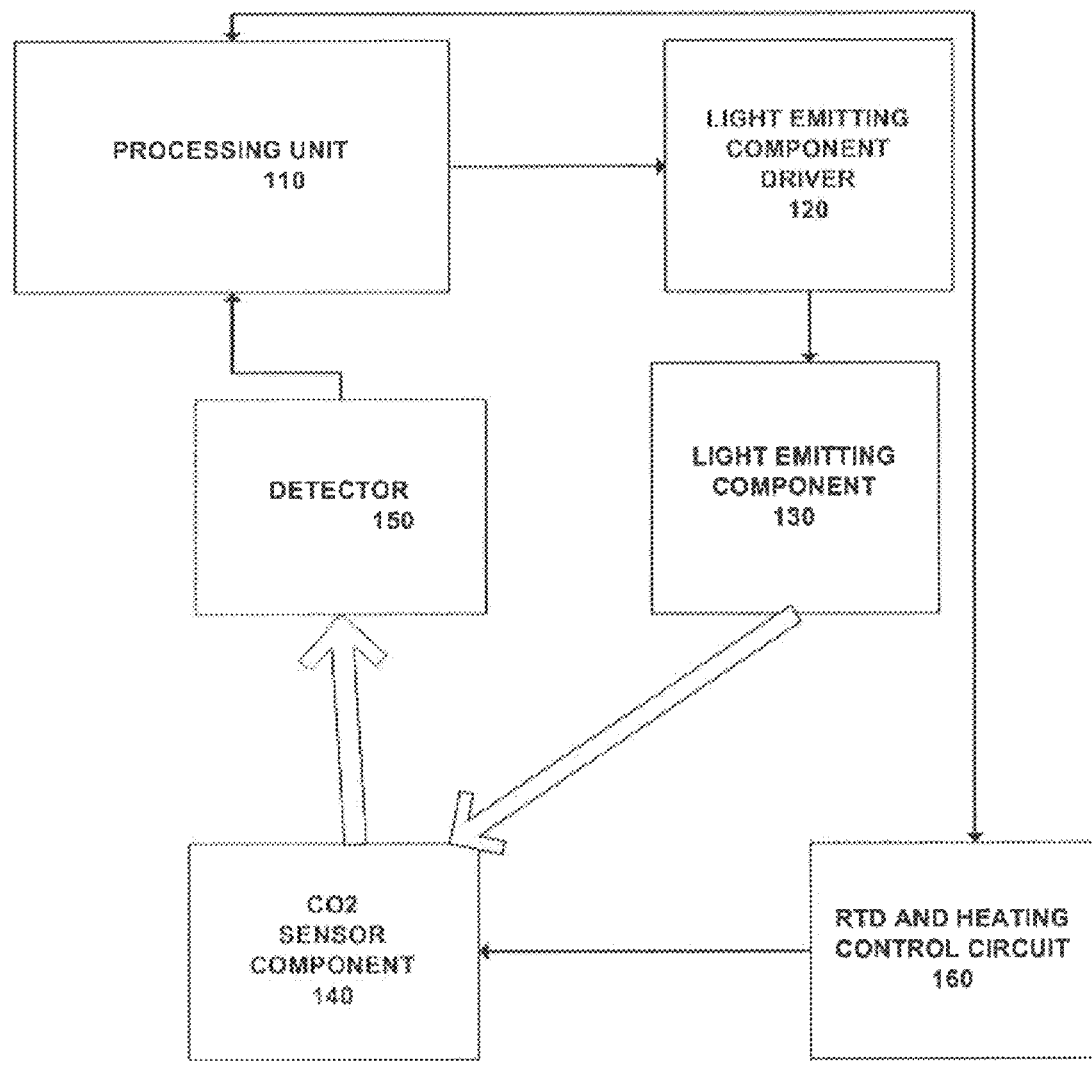

In one or more embodiments of the carbon dioxide detector system of these teachings, the range of wavelength includes a first and second predetermined wavelengths and the radiation emitted from the light emitting component 130 is scattered by the sensor component 140 (FIG. 2a, FIG. 2d). The first predetermined wavelength is substantially centered at a substantially strong absorption band of the absorption spectrum of the colorimetric indicator salt and the second predetermined wavelength is at a portion of the absorption spectrum of the colorimetric indicator salt where substantially no-absorbance is observed. In one embodiment, the carbon dioxide detector system of these teachings also includes a temperature sensor (160, FIG. 2d; such as a Resistive Temperature Detector (RTD)) and a heating component (160, FIG. 2d); the temperature sensor 160 and the heating component 160 being operatively connected to the sensor component 140 and a processing unit 110 configured to receive output from the detector component and the temperature sensor, to provide inputs to a driver 120 for the light emitting component and to the heating component 160, and to obtain a measurement of carbon dioxide concentration from the output from the detector component 140.

In one or more embodiments, the method of these teachings for forming a carbon dioxide detector includes mixing a colorimetric pH indicator, at a molar concentration for a desired colorimetric indicator salt, and a quaternary phosphonium hydroxide, at a slight molar excess, in a solvent, a transparent polymer vehicle or a plasticizer not being in a mixture with the colorimetric indicator salt, soaking a porous polymer membrane in the colorimetric indicator salt, quaternary phosphonium hydroxide, methanol solution for a predetermined length of time and evaporating the solvent.

In one instance, the solvent is an alcohol. In one specific instance, the solvent is methanol. In other instances, the solvent is acetone, methylethyl ketone (MEK), isopropyl alcohol (IPA), ethanol or dichloromethane.

In one embodiment, $CO_2$ sensing film of the sensor of these teachings is constructed by dip-coating a porous nylon membrane with a methanol solution containing the salt of a calorimetric pH indicator ($D^-$) and lipophilic phosphonium quaternary cation ($Q^+$). The salt forms by the reaction of acidic phenolic groups on the indicator with a hydroxide derivative of the quaternary phosphonium. The dip-coating process results in the indicator salt being deposited on the surface of the pore structure leaving the indicator salt available for direct interaction with $CO_2$ ($CO_2$ (g)) in the gaseous mixture within the pores of the porous membrane (nylon in one embodiment). The reversible interaction of the indicator salt with $CO_2$ results in a competitive displacement of the phosphonium cation from the weakly acidic indicator by the more acidic carbonic acid formed from the reaction of $CO_2$ with waters of hydration ($xH_2O$) associated with the indicator salt (see equilibrium expressions 2 and 3 below). Displacement of the phosphonium cation converts the first color (in one instance, blue) deprotonate form of the indicator to its second color (in one instance, yellow) protonated form (HD of equilibrium expression 4) producing a measurable shift in the optical absorption characteristics of the sensing membrane (see FIG. 5). The observed level of spectral shift is directly dependent upon the concentration of $CO_2$ thus enabling the detection of $CO_2$ from measurements of optical attenuation at specific wavelengths in the absorption spectrum of the indicator.

Equilibrium Expressions for $CO_2$ Sensing Chemistry:

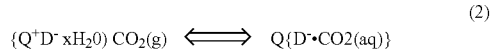

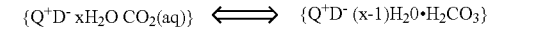

(In one instance Blue Yellow)

Exemplary embodiments are presented below in order to elucidate these teachings. It should be noted that these teachings are not limited only to the exemplary embodiments.

Exemplary Embodiment A

Early Warning Sensor (with Applications to Rebreather)

The sensor system consists of three main components, 1) sensor film, 2) sensor electronics, and 3) in-line flow-cell. The sensor system is designed to give a visual alarm (red flashing light) when CO2 level—exceed 1.4%.

Sensor Film

Figure 4:
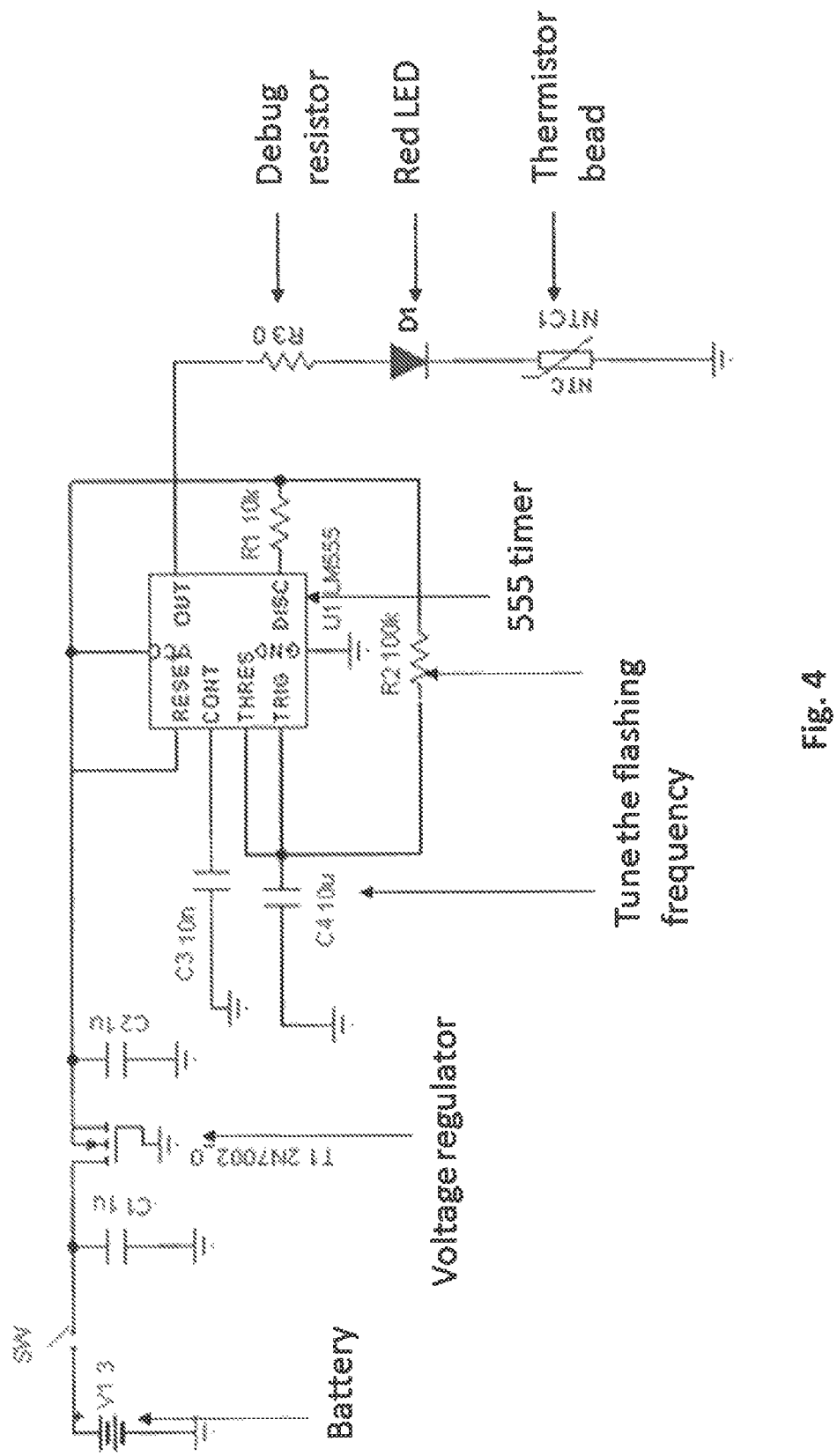
FIG. 4 shows a schematic circuit diagram representation for one exemplary embodiment of the carbon dioxide detection system of these teachings.

The sensing film of the sensor is based on a colorimetric $CO_2$ indicator salt formed from a quaternary phosphonium hydroxide and a weakly acidic phenolic-type pH sensitive dye, a transparent polymer vehicle or a plasticizer not being in a mixture with the colorimetric indicator salt. The indicator salt is immobilized in a highly porous polymeric membrane which allows $CO_2$ gas to rapidly diffuse into the membrane Electronics The electronics are designed to generate a flashing red light signal using a small light emitting diode (LED). The $CO_2$-sensing film is positioned over the red light emitting LED so that the light is only visible when the $CO_2$ level has shifted the indicator of the sensing film to its red-transmitting yellow form. A circuit diagram for the electronics is shown in FIG. 4. It includes the red LED, a 555 timer circuit, offset resistor and temperature sensitive thermistor bead. The drive voltage of LED) is modulated by a pulsed signal generated by the 555 timer circuit. The frequency and width of the pulse can be tuned by $C_4$ and $R_2$ of the RC network. The values of these components have been selected to give a pulse frequency 1 Hz, which is the same flashing frequency as a fire alarm. The NTC (negative temperature coefficient) thermistor bead and offset resistor are used to control the drive current of the LED, thus adjusting its output to match the temperature sensitivity of the CO2-sensing film. The simple design of the system electronics provides several advantages including low power consumption, compactness and low cost. The current demand of the fully functioning electronics is 0.62 mA which can be supplied by a single coin cell battery. The coil cell battery is directly soldered to the PCB. Battery life at drain level of 0.62 mA has been measured to be 75 hours (details described in the following). The compactness of the system electronics allow it to easily fit inside the flow cell with no obstruction of air flow. The third advantage, low cost, will allow the system electronics to be a single use disposable item thus simplifying service and increasing sensor reliability in each diving event.

Optimization of Sensor Film and Warning System

Sensor Film

The purpose of the sensor film is to control the light level transmitted between the LED and fiber optic cable of the system to provide an onset visible warning light level at 1.4%

$CO_2 \pm 0.1\%$. The working system employs a red warning LED selected to coincide with the maximum absorption band of $CO_2$-free form of the indicator. The three variables of interest in creating the optimum $CO_2$ sensor film are:

Selection of Porous Substrate. An appropriate porous substrate must offer:

High chemical resistance to withstand the strongly basic quaternary indicator salt High affinity for the indicator chemistry to yield a deeply colored sensor film Nylon offers the required affinity for the indicator salt and was selected as the material for this embodiment.

Selection of Indicator. The goal of indicator selection was to make the resulting film highly transmissive in response to $CO_2$ in the concentration range 0-2%. Selection of the proper colorimetric indicator was crucial to achieve this purpose. Of the various candidates studied, calorimetric pH indicators in the higher $pK_a$ range yielded the greatest change in transmission in the desired $CO_2$ concentration range. Thymol Blue ($pK_a$=8.9) and Xylenol Blue ($pK_a$=8.6) were the two candidates considered after initial screening due to their high $pK_a$ as compared to the other sulphonephthalein indicators. All other factors being equal (indicator concentration, film substrate and porosity), the effect of $pK_a$ is evident in transmission results vs. $CO_2$ concentration at 612 nm. Xylenol blue was chosen be the indicator for this embodiment as transmission results show that the warning light remains off at 1% $CO_2$ while showing a gradual turning on between 1 and 2% $CO_2$.

Hydrophobic Barrier. The ideal barrier film would allow rapid exchange of $CO_2$ between the sensing layer and the gas in the inhalation line, while blocking penetration of bulk water. Tyvek® 1073B was chosen as the hydrophobic barrier due to its high gas-permeability/bulk water impermeability. Tyvek® 1073B offered the highest water resistance of all commercially-available Tyvek® grades. Another favorable attribute of using Tyvek® was its ability to be heat sealed to polyolefin materials, allowing the sensor spot to be fully enclosed inside the barrier film via annular seal of the Tyvek® layer. The efficacy of the Tyvek® barrier was evaluated by applying a drop of bulk water to the sensing membrane while monitoring the optical transmission properties. This test was conducted with sensor films in the presence and absence of Tyvek®. The sample without the barrier showed abrupt transmission change while the sample with the barrier showed no change in optical throughput.

System Optimization to Warning System Target Level (1.4%)

Several variables were identified which would affect the first visible onset of the LED at 1.4% $CO_2$, which include:

1. Film porosity
2. Indicator concentration
3. LED output intensity

While all three factors have a direct impact on the resulting visual $CO_2$ response, the first two factors were considered above. For this reason, a substrate film with the largest pore size available, 20 microns, was selected to allow maximum light transmission compared with smaller pore materials, while also offering the fastest response time. Indicator concentration level was chosen based on previous optimization work to maximize sensitivity of response, approximately 6 mg/mL. Sensor chemistry dispensed at this level resulted in a uniformly deeply colored porous thin film. The factor that remained to adjust the onset of the diver warning system was therefore LED output intensity.

The first step in the system optimization was to determine the onset, or, turn-on point, of the LED warning system. The turn-on point was based on the visual acuity of a single test subject viewing the LED through a fiber optic cable in a dark room. Observing the light transmitted through the fiber, and adjusting the drive current on the power supply to modulate LED output, it was determined that the light was just visible at a level of 0.2 nW, which was determined to be the 'visible threshold,' and thus the onset of the visible warning system.

The above is an exemplary embodiment of the method of these teachings for detecting a carbon dioxide level in a gas in a substantially gastight loop which includes exposing the sensor component of these teachings to the gas; wherein presence of a predetermined amount of carbon dioxide in the gas causes a change in transmission of emission, transmitting radiation emitted from a light emitting device through the sensor component, the emission being in a range of wavelengths that is substantially peaked at one color, selecting the one color and the sensor component such that when the level of carbon dioxide in the gas is less than the predetermined amount of carbon dioxide, transmitted radiation at substantially the one color is substantially absorbed, and when the level of carbon dioxide is at least equal to the predetermined amount, transmitted radiation at substantially the one color is substantially unabsorbed, and indicating that the level of carbon dioxide in the gas is at least equal to the predetermined amount by transmission of radiation emitted from the light emitting device at the substantially one color.

In the exemplary embodiment, the colorimetric pH indicator is p-Xylenolsulfonephthalein (Xylenol Blue); and wherein the light emitting device is a red LED. As can be seen from FIG. 4, in one instance, the method also includes adjusting a current through the light emitting device in order to match temperature sensitivity of the sensor component.

Exemplary Embodiment B. Transcutaneous Sensor

An improved system for transcutaneous $CO_2$ sensing was developed by fabricating optical $CO_2$ sensor with very rapid response times compared with that of the traditional Severinghaus electrodes and identifying anatomical monitoring locations where tissue perfusion is less affected by shock and/or metabolic processes. Development of the rapid responding $CO_2$ sensor is expected to reduce the possibility of inaccuracies due to lag in the readings arising from slow sensor response.

Rapid response time $CO_2$ sensing film of the sensor of these teachings were constructed by the method disclosed hereinabove.

Figure 6:
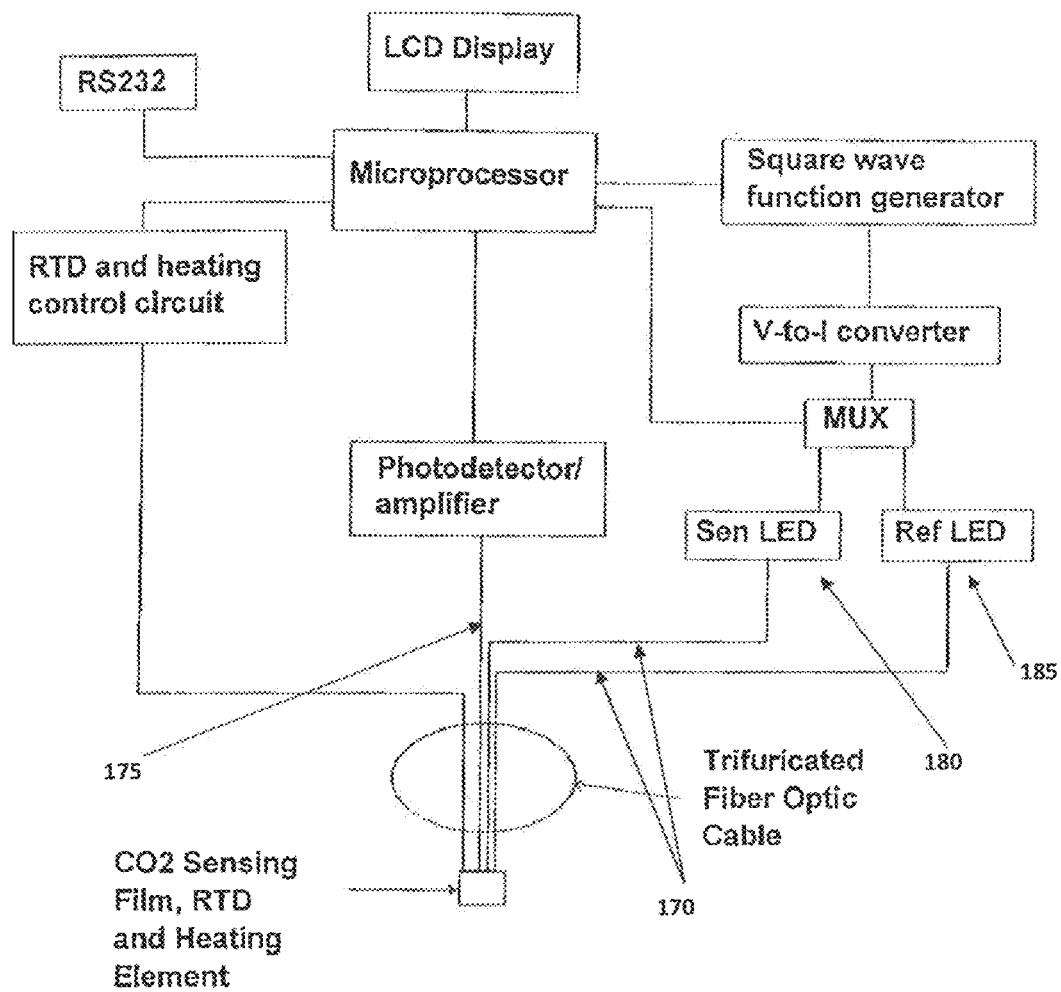
FIG. 6 is a flow diagram representation of another exemplary embodiment of the carbon dioxide detection system of these teachings.

A block diagram of the proposed transcutaneous CO2 sensor and electronics is shown in FIG. 6. The system electronics are based on a low power microprocessor which controls data collection, processing and display/transmission of calculated readings. Square wave voltage signals are converted to a modulated current signal which is sequentially directed to a pair of Light Emitting Diodes (LEDs) by way of an electronic multiplexer (MUX). LED light signals are transmitted via a trifurcated fiber optic cable which carries scatter light signals off the sensing film to a silicon photodiode photo detector/amplifier which will convert the optical signals to a modulate Voltage signal fed to the analog-to-digital converter of the TI microprocessor.

The embodiment shown in FIG. 6 includes a resistive temperature detector (RTD) and a heating element. In one instance, the heating element is a transparent thin-film resistive heating patch placed between the carbon dioxide sensor and the cable connection to the processing component ("microprocessor"). The heating element can include a controller component. A resistive temperature detector (in one exemplary instance, a 10 K thermistor) is, in one instance inserted underneath the heating element to monitor the temperature. In other embodiments, the resistive temperature detector or resistive thermometer can be placed in another location where monitoring the temperature is also possible.

In one embodiment, small, low power LEDs generate the sensing and reference light signals used to interrogate the status of the $CO_2$ sensing film. The LEDs provide emission at two wavelengths specific to the optical absorption properties of the indicator chemistry. (It should be noted that these same results can be obtained with a light emitting component, such as a white LED, where the emission of the light emitting component has a spectrum including the two wavelengths.) One of the selected wavelengths of light (Sen LED) is centered over the strongest absorption band of the indicator while the second is from a portion of the spectrum where no absorbance is observed (Ref LED) and is used as a reference to normalize for variations in optical signal strength due to changes in the optical transmission properties of the fiber optic cable and/or variations in the gain of the detector amplifier circuit due to temperature and aging. Measurements of the CO2-dependent optical signal strengths are made by sequentially firing the LEDs into two of the three legs of the trifurcated fiber optic cable. A portion of the LED light signals is scattered off the sensing film and captured by the third leg of fiber cable which terminates at a silicon photodiode within the optoelectronics assembly.

The embodiment shown in FIG. 6 is an exemplary of a carbon dioxide detection system that includes a first optical transmission component 170 receiving the radiation emitted by the light emitting component and transmitting the radiation emitted by the light emitting component to the sensor component and a second optical transmission component 175 receiving radiation scattered from the sensor component and transmitting the radiation scattered from the sensor component to the detector component and where the light emitting component includes a first light emitting device 180 emitting radiation at the first predetermined wavelength and a second light emitting device 185 emitting radiation at the second predetermined wavelength.

Optical signals at the silicon photodetector are converted to voltage signals and amplified by a high-gain transimpedance amplifier circuit prior to being fed into the analog-to-digital converter of a microprocessor controller which accumulates readings of the voltage signal for the predetermined sampling period of the LED. A similar measurement is taken of background optical signal strength by sampling the signal from the photodetector with both LEDs off. The background signal contribution is subtracted from the signal values acquired from the two LEDs and a ratio of the resulting background corrected signals calculated from which calibration expressions are used to calculate reads $CO_2$ concentration. Control of the sampling frequency, LED pulse duration and signal averaging are all controlled by user defined setting in the firmware of the microprocessor. This simplifies optimization of sensor performance and utilization of battery power.

Figure 7:
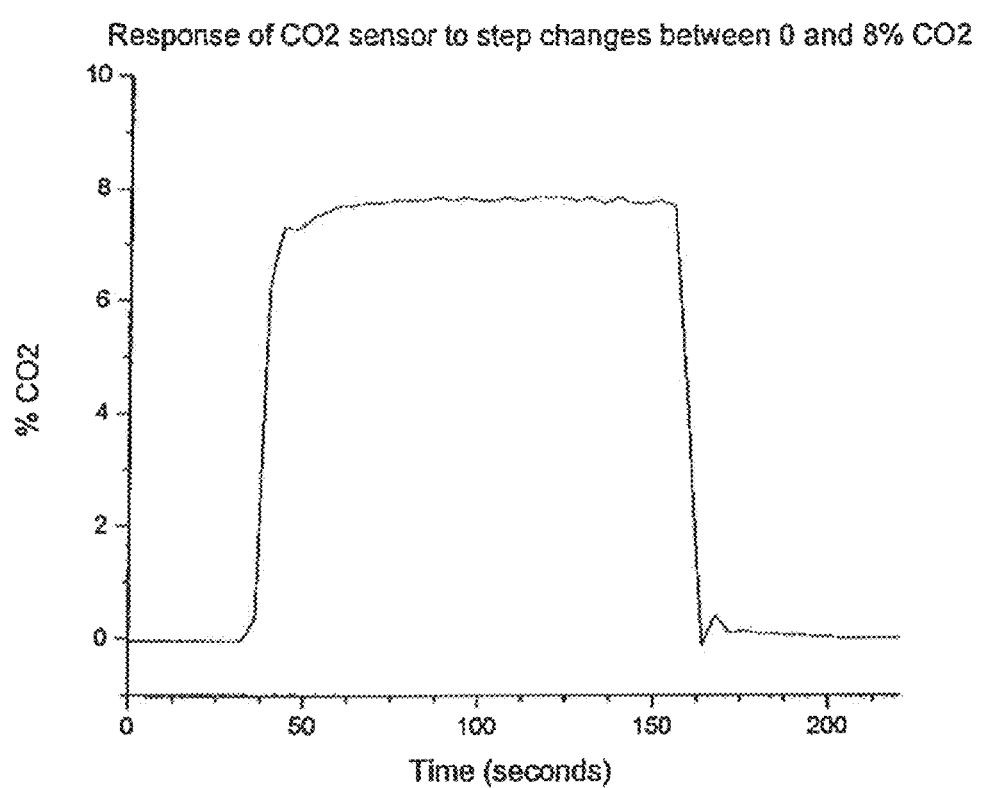
FIG. 7 is a graphical representation of the carbon dioxide sensor response to step changes in gaseous $CO_2$, for one embodiment of the carbon dioxide sensor of these teachings.

The transducer portion of the sensor consists of the colorimetric $CO_2$ sensing membrane, a resistive heating element and RTD temperature sensor. In this embodiment, the $CO_2$ sensing film is configured within an envelope consisting of a porous polypropylene top layer (Tyvek) and a transparent, non porous low density polyethylene bottom layer (LDPE) formed by an annular heat seal around a disk of the sensing membrane (see FIGS. 3a, 3b). The envelope is designed to protect the sensing film from direct interaction with bulk water, which could interfere with the detection mechanism, but still allow for rapid exchange of gases between the sensing film and surrounding gas sample. The effectiveness of the approach is illustrated in the response plot of FIG. 7, which shows the response of the sensor to step changes in $CO_2$. The sensor envelope response time is estimated to be 8 to 10 seconds following either an increasing and decreasing change in $CO_2$. The rapid response of the $CO_2$ sensor of these teachings is expected to substantially eliminate the time lag in the readings with the slower responding transcutaneous $CO_2$ electrode that are currently available enabling better agreement with BGA readings during periods of change in arterial $CO_2$.

Identifying the indicator salt and loading level which, when immobilized in the porous nylon film, shows optimal signal attenuation over the $CO_2$ partial pressure range 10 to 70

Figure 8:
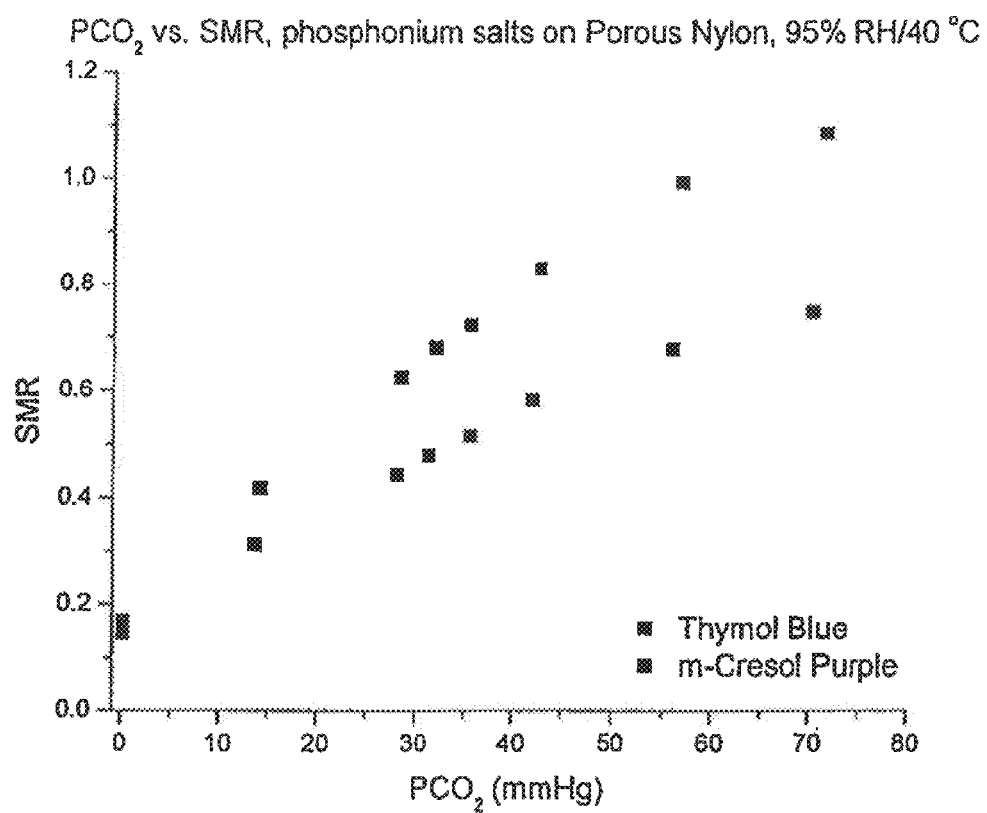
FIG. 8 is a graphical representation of optical readings versus PCO2 for colorimetric phosphonium salts of these teachings.

The indicator salt and loading level that is used to construct the transcutaneous $CO_2$ sensor is selected to ensure a range of response that is consistent with arterial blood gas values, which is presumed to be between 10 to 80 nunHg. While not desiring to be bound by theory, in one explanation, the range of response for the indicator chemistry of the optical CO2 sensor is largely dictated by the pKa of the phenolic group on the indicator used to form the $CO_2$ sensitive phosphonium salt. The pKa of pH indicators is defined as the midpoint in the response of the indicator to pH. Phosphonium salts of low pKa pH indicators are less reactive toward CO2 and as such show a response over a wider range of $CO_2$. For example, the desired range of operation for the rebreather sensor is 0 to 3%. The ideal indicator for this shallow range of operation is one with a relatively high pKa (8.6-9.0, very weakly acidic phenol) enabling facile displacement of the phosphonium cation under exposure of the sensor to low $CO_2$ concentrations. Optical responses of films containing the phosphonium salts of Thymol Blue (pKa 8.6) and meta Cresol Purple (pKa 8.2) immobilized in porous nylon membranes show the signal magnitude ratio (SMR) for the sensing and reference LED signals reflected off the sensing film samples. As is seen in the plot of FIG. 8, the indicator response of the meta Cresol Purple salt shows lower sensitivity over the range 0 to 8% $CO_2$ compared with that of the higher pKa Thymol Blue.

The indicator for the transcutaneous $CO_2$ sensor is selected based on response data collected from nylon films containing the phosphonium salts of the pH indicators shown in Table 1. All of these indicators are phenolsulphophthalein type indicator which exhibit colorimetric shifts from blue to yellow upon protonation. The indicators selected for testing have pKa values in the range 7.0 to 8.9 (see Table 1) which provide for a wide range of sensitivity and degree of curvature in the plots of their response. Phosphonium salt solutions of each indicator were formed by mixing the indicator (6 mg/ml) with a slight molar excess of tetraoctyl phosphonium hydroxide in methanol. Individual samples of porous nylon film were stained with the indicator salts by soaking for 2 minutes in the methanol solutions followed by evaporation of the methanol in air.

TABLE 1

Candidate indicators for $CO_2$ sensitive phosphonium salt

| Indicator | Ka |
|---|---|
| Xylanol Blue | 8.9 |
| Thymol Blue | 8.6 |
| Meta Cresol Purple | 8.2 |
| Cresol Red | 7.7 |
| Bromoyhymol Blue | 7.0 |

The above is an exemplary embodiment of the method of these teachings for arterial carbon dioxide level detection which includes placing the sensor component of these teachings on the epidermis of a subject, scattering radiation emitted from a light emitting device through the sensor component, wherein a range of wavelengths of radiation emitted by the light emitting device includes a first and second predetermined wavelengths; wherein the first predetermined wavelength is substantially centered at a substantially strong absorption band of the absorption spectrum of the colorimetric indicator salt, wherein the second predetermined wavelength is at a portion of said absorption spectrum where substantially no-absorbance is observed and wherein presence of a predetermined amount of arterial carbon dioxide causes a change in transmission of emission, detecting scattered radiation at the first and second predetermined wavelengths, obtaining a ratio of detected scattered radiation at the first wavelength to detected scattered radiation at the second wavelength and determining carbon dioxide partial pressure from the ratio. In one instance, the method also includes subtracting a background detected radiation from the detected scattered radiation at the first wavelength and from the detected scattered radiation at the second wavelength before taking the ratio.

It should be noted that these teaching are not limited to only the exemplary embodiment.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Although the invention has been described with respect to various embodiments, it should be realized these teachings are also capable of a wide variety of further and other embodiments within the spirit and scope of the appended claims.

What is claimed is:

1. A carbon dioxide detector comprising:
    a sensor component comprising:
        a colorimetric indicator salt of a colorimetric pH indicator and a lipophilic phosphonium quaternary cation, wherein a transparent polymer vehicle or a plasticizer is not used; and
        a porous membrane; the colorimetric indicator salt being deposited on a surface of a pore structure of the porous membrane; the colorimetric indicator salt deposited on the porous membrane does not include a transparent polymer vehicle or a plasticizer; the sensor component being configured such that a response ("rise") time and a recovery ("fall") time of the carbon dioxide detector are substantially similar; the pore structure and a concentration of the colorimetric indicator salt in a solution being configured to result in a thin film of the colorimetric indicator salt being deposited on the porous membrane.

2. The carbon dioxide detector of claim 1 wherein the response ("rise") time and the recovery ("fall") time of the carbon dioxide detector is between about 7 to about 10 seconds.

3. The carbon dioxide detector of claim 1 further comprising:
    a hydrophobic barrier; the sensor component being disposed on the hydrophobic barrier.

4. The carbon dioxide detector of claim 3 further comprising:
    a substantially non-porous layer disposed on the hydrophobic barrier and surrounding the sensor component.

5. The carbon dioxide detector of claim 4 wherein the substantially non-porous layer comprises low-density polyethylene.

6. The carbon dioxide detector of claim 3 wherein the hydrophobic barrier comprises a nonwoven layer of spunbond olefin fibers.

7. The carbon dioxide detector of claim 1 wherein the colorimetric pH indicator is thymolsulfonephthalein (Thymol Blue), m-cresolsulfonephthalein (Meta Cresol purple), o-cresolsulfonephthalein (Cresol Red), bromothymol sulfone phthalein (Bromothymol Blue) or p-Xylenolsulfonephthalein (Xylenol Blue).

8. The carbon dioxide detector of claim 1 wherein the lipophilic phosphonium quaternary cation originates from a quaternary phosphonium hydroxide.

9. The carbon dioxide detector of claim 1 wherein the porous membrane is a polymer membrane.

10. The carbon dioxide detector of claim 9 wherein the porous membrane is a nylon membrane.

11. A carbon dioxide detection system comprising:
    a light emitting component emitting radiation at a range of wavelengths;
    the carbon dioxide detector of claim 3 wherein the sensor component is disposed to receive the radiation emitted by the light emitting component; the range of wavelengths being selected to include wavelengths in an absorption spectrum of the colorimetric indicator salt; and a detector component configured to receive radiation after an interaction with the sensor component; wherein presence of a predetermined amount of carbon dioxide in ambient causes a change in spectral properties of the colorimetric pH indicator.

12. The carbon dioxide detection system of claim 11 wherein emission in the range of wavelengths is substantially peaked at one color; wherein the interaction is transmission through the sensor component; wherein the carbon dioxide detector is disposed above the light emitting component; the carbon dioxide detector being in substantially unobstructed optical communication with the light emitting component; wherein presence of a predetermined amount of carbon dioxide in the ambient causes a change in transmission of emission from the light emitting component.

13. The carbon dioxide detection system of claim 12 further comprising:
    a driver circuit providing a driving voltage for the light emitting component; and a negative temperature coefficient thermistor component operatively connected to the light emitting component and configured to adjust a current through the light emitting component to match temperature sensitivity of the carbon dioxide detector.

14. The carbon dioxide detection system of claim 12 wherein the change in transmission causes the emission from the light emitting component to be substantially unabsorbed by the carbon dioxide detector; and wherein the light emitting component illuminates, through the carbon dioxide detector, a fiber-optic cable, the fiber-optic cable propagating the emission of the light emitting component.

15. The carbon dioxide detection system of claim 12 wherein the colorimetric pH indicator is p-Xylenolsulfonephthalein (Xylenol Blue); and wherein the light emitting component is a red LED.

16. The carbon dioxide detection system of claim 11 wherein the range of wavelengths includes a first and second predetermined wavelength.

17. The carbon dioxide detection system of claim 16 wherein the interaction is scattering from the sensor component; wherein the first predetermined wavelength is substantially centered at a substantially strong absorption band of the absorption spectrum of the colorimetric indicator salt; wherein the second predetermined wavelength is at a portion of said absorption spectrum where substantially no-absorbance is observed; and wherein the carbon dioxide detection system further comprises:
a temperature sensor;
a heating component; the temperature sensor and the heating component being operatively connected to the sensor component; and
a processing unit configured to receive output from the detector component and the temperature sensor, to provide inputs to a driver for the light emitting component and to the heating component, and to obtain a measurement of carbon dioxide concentration from the output from the detector component.

18. The carbon dioxide detection system of claim 16 wherein the carbon dioxide detector further comprises a substantially non-porous layer disposed on the hydrophobic barrier and surrounding the sensor component; and wherein the substantially non-porous layer comprises low-density polyethylene; and wherein the hydrophobic barrier comprises a nonwoven layer of spunbond olefin fibers.

19. The carbon dioxide detection system of claim 11 wherein the colorimetric pH indicator is thymolsulfonephthalein (Thymol Blue), m-cresolsulfonephthalein (Meta Cresol purple), o-cresolsulfonephthalein (Cresol Red), bromothymol sulfone phthalein (Bromothymol Blue) or p-Xylenolsulfonephthalein (Xylenol Blue).

20. The carbon dioxide detection system of claim 16 further comprising:
a first optical transmission component receiving the radiation emitted by the light emitting component and transmitting the radiation emitted by the light emitting component to the sensor component; and
a second optical transmission component receiving radiation scattered from the sensor component and transmitting the radiation scattered from the sensor component to the detector component.

21. The carbon dioxide detection system of claim 16 wherein the light emitting component comprises:
a first light emitting device emitting radiation at the first predetermined wavelength; and
a second light emitting device emitting radiation at the second predetermined wavelength.

22. A method for forming a carbon dioxide detector, the method comprising: mixing a colorimetric pH indicator at a molar concentration for a desired colorimetric indicator salt, and a quaternary phosphonium hydroxide, at a slight molar excess, in a solvent; a transparent polymer vehicle or a plasticizer not being in a mixture with the colorimetric indicator salt; soaking a porous membrane in the colorimetric pH indicator, quaternary phosphonium hydroxide, solvent solution for a predetermined length of time; and evaporating the solvent to form a thin film.

23. The method of claim 22 wherein the solvent is an alcohol.

24. The method of claim 23 wherein the alcohol is methanol.

25. The method of claim 22 wherein the colorimetric pH indicator is thymolsulfonephthalein (Thymol Blue), m-cresolsulfonephthalein (Meta Cresol purple), o-cresolsulfonephthalein (Cresol Red), bromothymol sulfone phthalein (Bromothymol Blue) or p-Xylenolsulfonephthalein (Xylenol Blue).

26. The method of claim 22 wherein the quaternary phosphonium hydroxide is tetraoctyl phosphonium hydroxide.

27. The method of claim 22 wherein the porous membrane is a porous polymer membrane.

28. The method of claim 27 wherein the porous polymer membrane is a nylon membrane.

29. A method for detecting a carbon dioxide level in a gas in a substantially gastight loop, the method comprising:
exposing the sensor component of claim 3 to the gas;
transmitting radiation emitted from a light emitting device through the sensor component; emission being in a range of wavelengths that is substantially peaked at one color; wherein presence of a predetermined amount of carbon dioxide in the gas causes a change in transmission of emission;
selecting the one color and the sensor component such that when a level of carbon dioxide in the gas is less than the predetermined amount of carbon dioxide, transmitted radiation at substantially the one color is substantially absorbed, and when the level of carbon dioxide is at least equal to the predetermined amount, transmitted radiation at substantially the one color is substantially unabsorbed; and
indicating that the level of carbon dioxide in the gas is at least equal to the predetermined amount by transmission of radiation emitted from the light emitting device at the substantially one color.

30. The method of claim 29 wherein the colorimetric pH indicator is p-Xylenolsulfonephthalein (Xylenol Blue); and wherein the light emitting device is a red LED.

31. The method of claim 29 further comprising adjusting a current through the light emitting device in order to match temperature sensitivity of the sensor component.

32. A method for arterial carbon dioxide level detection comprising:
placing the sensor component of claim 4 on an epidermis of a subject ; wherein presence of a predetermined amount of arterial carbon dioxide causes a change in absorbance of emission;
scattering radiation emitted from a light emitting device through the sensor component; wherein a range of wavelengths of radiation emitted by the light emitting device includes a first and second predetermined wavelength; wherein the first predetermined wavelength is substantially centered at a substantially strong absorption band of an absorption spectrum of the colorimetric indicator salt; wherein the second predetermined wavelength is at a portion of said absorption spectrum where substantially no-absorbance is observed;
detecting scattered radiation at the first and second predetermined wavelengths;
obtaining a ratio of detected scattered radiation at the first wavelength to detected scattered radiation at the second wavelength; and
determining carbon dioxide partial pressure from the ratio.

33. The method of claim 32 further comprising subtracting a background detected radiation from the detected scattered radiation at the first wavelength and from the detected scattered radiation at the second wavelength.

* * * * *